United States Patent
Romero

(10) Patent No.: US 8,357,142 B2
(45) Date of Patent: Jan. 22, 2013

(54) CONNECTOR HUB ASSEMBLY

(75) Inventor: Paul R. Romero, Loveland, CO (US)

(73) Assignee: Covidien LP, Mansfield, MA (US)

( * ) Notice: Subject to any disclaimer, the term of this patent is extended or adjusted under 35 U.S.C. 154(b) by 1009 days.

(21) Appl. No.: 12/250,077

(22) Filed: Oct. 13, 2008

(65) Prior Publication Data
US 2010/0094263 A1    Apr. 15, 2010

(51) Int. Cl.
- A61M 25/16    (2006.01)
- A61M 25/18    (2006.01)
- A61M 39/00    (2006.01)
- A61M 39/10    (2006.01)

(52) U.S. Cl. .................................................. 604/533

(58) Field of Classification Search .......... 604/174–180, 604/410, 533–539
See application file for complete search history.

(56) References Cited

U.S. PATENT DOCUMENTS

| | | | |
|---|---|---|---|
| 3,682,180 A * | 8/1972 | McFarlane | 604/174 |
| 3,895,635 A | 7/1975 | Justus et al. | |
| 4,419,998 A | 12/1983 | Heath | |
| 5,190,525 A * | 3/1993 | Oswald et al. | 604/83 |
| 5,205,530 A * | 4/1993 | Fish | 248/690 |
| 5,268,982 A | 12/1993 | Schaffer et al. | |
| 5,399,172 A * | 3/1995 | Martin et al. | 604/248 |
| 5,695,088 A * | 12/1997 | Kasbohm | 220/495.11 |
| 5,702,428 A | 12/1997 | Tippey et al. | |
| 5,865,741 A | 2/1999 | Kelly et al. | |
| D448,345 S | 9/2001 | Fristedt | |
| D478,321 S | 8/2003 | Peng | |
| 6,662,056 B2 | 12/2003 | Picardo et al. | |
| 6,786,743 B2 | 9/2004 | Huang | |
| 6,824,422 B2 | 11/2004 | Huang | |
| D515,412 S | 2/2006 | Waaler et al. | |
| D516,028 S | 2/2006 | Deng | |
| D521,856 S | 5/2006 | Waaler et al. | |
| 7,131,860 B2 | 11/2006 | Sartor et al. | |
| D556,134 S | 11/2007 | Lee et al. | |
| 7,416,437 B2 | 8/2008 | Sartor et al. | |
| D578,065 S | 10/2008 | Baker et al. | |
| D580,370 S | 11/2008 | Ramsey | |
| D583,770 S | 12/2008 | Ramsey | |
| D593,491 S | 6/2009 | Liu et al. | |
| 2005/0113818 A1 * | 5/2005 | Sartor et al. | 606/34 |
| 2009/1024801 | 10/2009 | Heard et al. | |

* cited by examiner

Primary Examiner — Matthew F Desanto

(57) ABSTRACT

The present disclosure relates to a connector hub assembly. The connector hub assembly includes a housing and a retention device. The housing has a connector bank having one or more input ports and one or more output ports, that are defined therein. The input ports are configured to operably connect to one or more first conduits and the output ports are configured to operably connect to one or more second conduits. The retention device is operably coupled to the housing. The retention device includes a flexible membrane that has one or more slits defined therethrough that form flexible segments in the membrane. The flexible segments are configured to selectively secure the connector hub assembly to a sheet-like material when the sheet-like material is fed through the slits.

13 Claims, 3 Drawing Sheets

CONNECTOR HUB ASSEMBLY

BACKGROUND

1. Technical Field

The present disclosure relates to surgical connector hubs. More particularly, the present disclosure relates to a connector hub assembly having a selectively engageable retention device to facilitate cable retention in an operating theater.

2. Description of Related Art

Typically in the medical field, particularly in the patient monitoring sector, a connector hub, which is also known as a connector bank, is commonly used in the medical field and is configured to join multiple conduits into one central distribution unit. The conduits typically include electrical components (e.g., EKG wiring, heart monitoring wire leads, etc.) disposed therein and/or other components (e.g., pneumatic passages, mechanical lines, etc.). The conduits are connected to the connector hub via various connectors that are received within receptacles of the connector hub. In most scenarios, the connector hub is conveniently located near the patient.

During surgery and/or other medical treatments, a clinician is inclined to make quick and efficient connections near the patient, while at the same time, trying not to disturb or hurt the patient. Placing the connector bank far from the patient would be inconvenient for the clinician and the patient. Thus, the hub connector is typically positioned near and/or on the patient, for example, attaching the connector hub to the patient's gown, via a separate attaching device, for example, a surgical clip, an adhesive material, and/or hoop and loop fasteners. There are, of course, drawbacks in using a separate attaching device to attach the hub connector near the patient, such as, simply losing the secondary attaching device and/or, in some cases, the secondary attaching device not functioning properly. These drawbacks leave the clinician, in the midst of a medical treatment, to allow the hub connector to hang freely from the conduits, in which the connector hub is connected thereto. This results to an increased risk of damaging the conduit connections and/or discomforting the patient, which can possibly lead to unsuccessful medical treatment for the patient.

SUMMARY

The present disclosure relates to a connector hub assembly. The connector hub assembly includes a housing and a retention device. The housing has a connector bank having one or more input ports and one or more output ports, that are defined therein. The input ports are configured to operably connect to one or more first conduits and the output ports are configured to operably connect to one or more second conduits. The retention device is operably coupled to the housing. The retention device includes a flexible membrane that has one or more slits defined therethrough that form flexible segments in the membrane. The flexible segments are configured to selectively secure the connector hub assembly to a sheet-like material when the sheet-like material is fed through the slits.

In embodiments, the housing may include a top portion and a bottom portion. The top portion may include the retention device and the bottom portion may include the connector bank. The flexible membrane includes one or more slits forming a corresponding number of flexible segments. In addition, the flexible membrane may be selectively engageable with the housing.

In embodiments, the top portion and the bottom portion may be monolithically formed into a one-piece configuration. Alternatively, the top portion and the bottom portion may be operably coupled by injection molding, gluing, snap fitting, hook or press forming. The housing may be constructed from a plastic material or a metallic material.

The first conduits and/or the second conduits may be energy-transporting conduits, air-transporting conduits, or fluid-transporting conduits. Also, the input and output ports may be operably connected to the first and/or second conduits by quick-release-type connectors, luer-type connectors, detent-type connectors, screw-type connectors, or bayonet-type connectors.

In embodiments, the housing may further include a finger grip for manipulating the connector hub assembly. The retention device includes a membrane having a central aperture defining the slits. The slits extend radially outwards from the central aperture towards an outer bead to form a corresponding number of flexible segments for receiving the sheet-like material. The outer bead is operably coupled to a retaining ring that is disposed within the housing. The membrane may be formed from a carbon fiber composites, plastic composites, flexible material composites, or epoxy composites. In addition, the retention device may be formed in a circular shape, a square shape, an elongate shape, a triangular shape, or a polygonal shape.

In other embodiments, the slits are formed in a serpentine manner within the flexible membrane to define one or more opposing flexible finger-like elements therewithin for engaging the sheet-like material when the sheet-like material is fed therethrough.

DETAILED DESCRIPTION

Particular embodiments of the present disclosure, namely, the connector hub assembly, are described hereinbelow with reference to the accompanying drawings. In the following description, well-known functions or constructions are not described in detail to avoid obscuring the present disclosure in unnecessary detail. As used herein and as is traditional, the term "distal" refers to the portion that is furthest from the user/clinician and the term "proximal" refers to the portion that is closest to the user/clinician. In addition, terms such as "above", "below", "top", "bottom", etc. refer to the orientation of the figures or the direction of components and are simply used for convenience of description.

Figure 1:
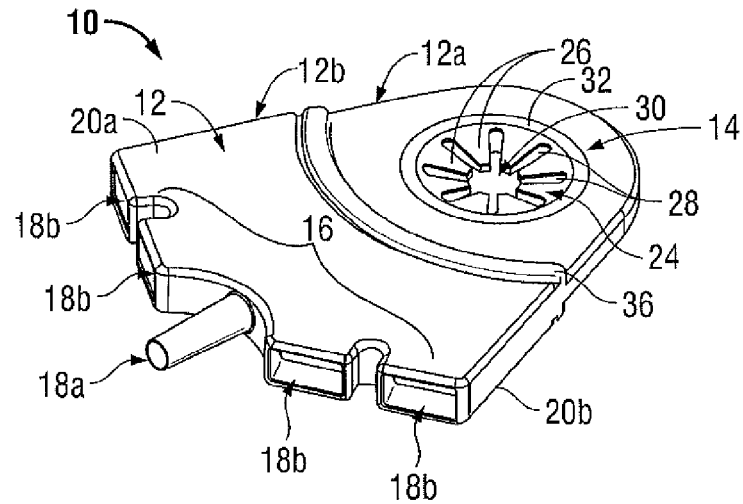
FIG. 1. is a front, perspective view of the connector hub assembly having a retention device according to one embodiment of the present disclosure.

Referring initially to FIG. 1, a connector hub assembly is generally depicted as reference numeral 10. Connector hub assembly 10 includes a housing 12 having a top portion 12a and a bottom portion 12b. The top portion 12a and the bottom portion are monolithically formed to each other. In other embodiments, the top portion 12a and the bottom portion 12b may be separate components such that top portion 12a and bottom portion 12b may be operably coupled to each other. In this instance, a clinician or surgeon may opt to selectively engage a particular bottom portion to engage particular cabling or conduits. In addition, the clinician may opt for a different engagement portion, e.g., top portion 12a, due to a particular operating environment. Housing 12 may be constructed, but not limited, from a durable plastic material, a metallic material, or any other durable housing material.

The top portion 12a includes a pull-through retention device 14 that is configured to selectively attach the connector hub assembly 10 at a desired location that is convenient for the user and/or the patient. The pull-through retention device 14 is described in further detail below. Bottom portion 12b of housing 12 includes a connector bank 16 configured to allow selective engagement of multiple conduits and/or wires into a corresponding location defined thereon. For example, connector bank 16 includes one or more input ports 18a and one or more output ports 18b, or vice versa. The connector bank 16 allows the input ports 18a and output ports 18b to be operably coupled to each other in a predetermined arrangement. The multiple conduits allow selective coupling of electrical and/or mechanical conduits 19a and 19b (shown in FIG. 2).

Figure 2:
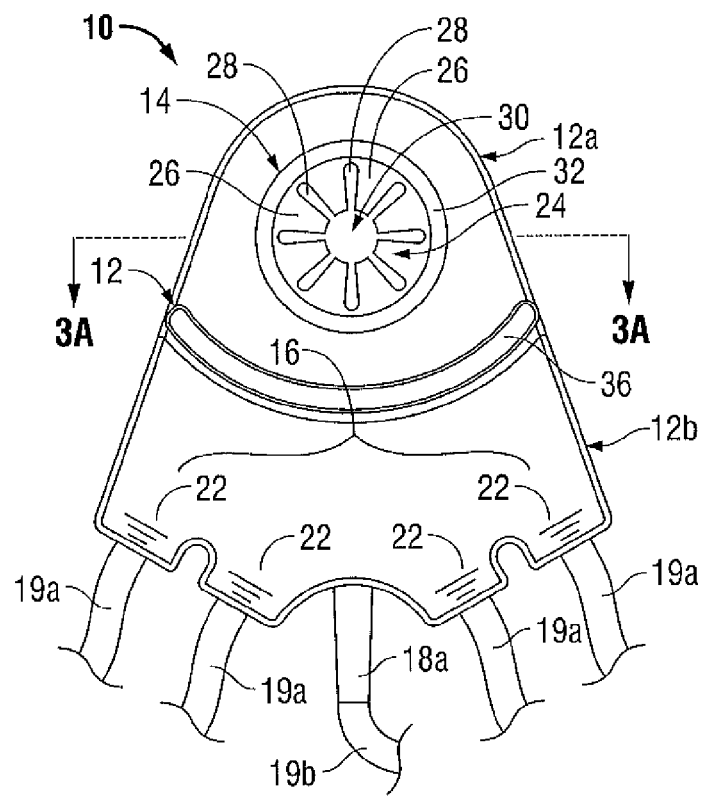
FIG. 2. is a top view of the connector hub assembly of FIG. 1.
Figure 3A:
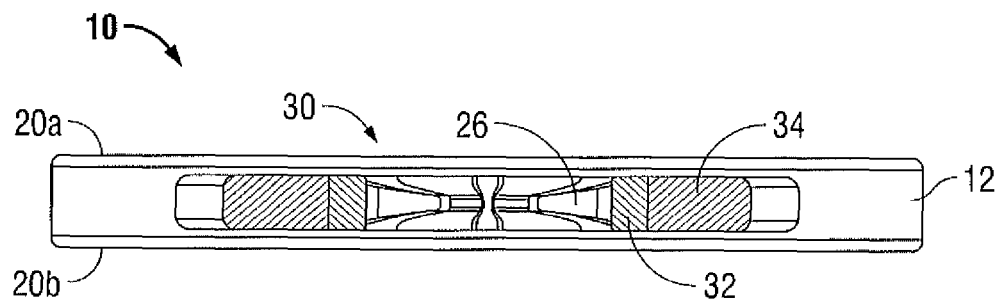
FIG. 3A is a side, cross-sectional view of the connector hub assembly of FIG. 1.

In an exemplary embodiment, shown in FIGS. 1-3, input port 18a is disposed centrally on the bottom portion 12b of the housing 12. Bottom portion 12b may be configured to be selectively and mechanically coupled to an external device (not shown). The external device may be, for example, but is not limited to, an electrosurgical generator, heart monitoring device, pulmonary monitoring device, or any other medical device and/or instrument adapted to be utilized with connector bank 16. Also shown in FIGS. 1-3, output ports 18b are also disposed on the bottom portion 12b of the housing 12. Output ports 18b are disposed on both sides of input port 18a. The locations of the input and output ports 18a and 18b, respectively, may be disposed at any location on the housing 12.

Different types of input and output conduits 19a and 19b, respectively, may be operably coupled to the one or more corresponding input and output ports 18a and 18b, respectively. For example, energy-transporting conduits, (e.g., EKG wires, electrical wires, etc.) may be utilized and operably coupled in the one or more ports 18a and 18b. Additionally or alternatively, air-transporting or fluid-transporting conduits may be operably coupled to the one or more input and output ports 18a and 18b, respectively. Input and output conduits 19a and 19b may be operably coupled to input and output ports, 18a and 18b, by any type of coupling means, for example, but not limited to, quick-release-type connectors, luer-type connectors, detent-type connectors, screw-type connectors or bayonet-type connectors.

As shown in FIG. 2, housing 12 may include indicia 22 disposed on portion 12b and a finger grip 36 to facilitate handling during use of connector 10. Indicia 22 may be disposed on any side of the bottom portion 12b (e.g., front side 20a). Additionally or alternatively, indicia 22 may be monolithically formed upon fabrication of the housing 12, or in the alternative, may be marked by a suitable marking means (e.g., stickers, laser etchings, etc.). Indicia 22 may represent to the user numbers, letters, words, symbols, pictures, or any other accommodating marking above the respective port assigned. For example, indicia 22 may indicate to a user an input port with the word of "in" and an output port with the word "out."

Finger grip 36 is disposed on the housing 12 to allow the user to firmly hold the connector hub assembly 10, while manipulating the connector bank 16 around the patient. The finger grip 36 also allows the user to comfortably grip the connector bank 16 to facilitate firmly attaching and detaching the multiple conduits from input and output ports, 18a and 18b, respectively.

As mentioned above, housing 12 further includes a pull-through retention device 14 configured to retain a material "M" as it is passed therethrough. Retention device 14 includes a membrane 24 formed from a thin flexible material (e.g., carbon fiber composites, plastic composites, flexible material composites, composite epoxies, elastomers, etc.). Membrane 24 is provided with a central aperture 30 and a plurality of spaced slits 28. Slits 28, which may be equally spaced, extend radially outwardly from the central aperture 30 towards an outer bead 32 to form a plurality of flexible segments 26. A retaining ring 34 (see FIG. 3A, 3B) is enclosed within the housing 12 and is configured to secure membrane 24 within retention device 14 by mechanically coupling to outer bead 32 of membrane 24. As mentioned above, different types of retention devices may be selectively coupled to the housing 12 depending upon a particular purpose.

Figure 3B:
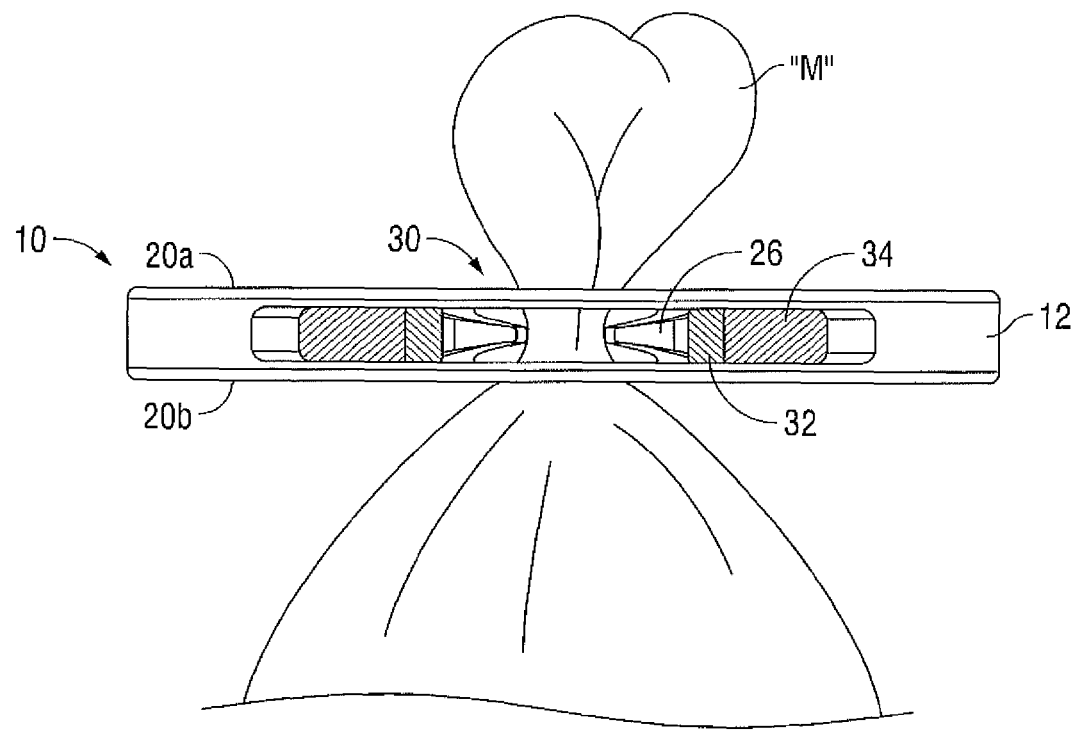
FIG. 3B is a side, cross-sectional view of the connector hub assembly of FIG. 1 showing the retention device having a material pulled therethrough.

In use, material "M" is inserted through membrane 24 of retention device 14, for example, through the central aperture 30 from the back side 20b of connector bank assembly 10. Material "M" may be, for example, a patient's gown, a bed sheet, medical drapery, or any other type of fabric within the vicinity of the patient. Referring to FIG. 3B, as material "M" is inserted through central aperture 30, material "M" is further pulled from the front side 20a through central aperture 30 such that segments 26 are forced in the same direction the material "M" is being pulled through. As the user pulls the material "M" taut, this substantially secures the connector hub assembly 10 to the material "M", thus causing the flexible segments 26 between slits 28 to flex in the direction of the inserted material "M". Segments 26 thereby grip and secure material "M" within the central aperture 30, thus operably coupling connector hub assembly 10 near the patient.

Figure 4:
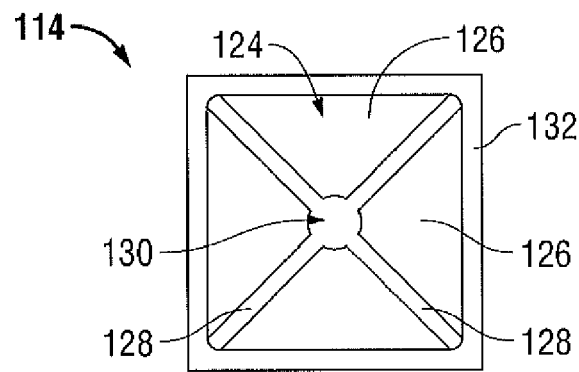
FIG. 4 is a top view of another embodiment of the retention device in accordance with the present disclosure.
Figure 5:
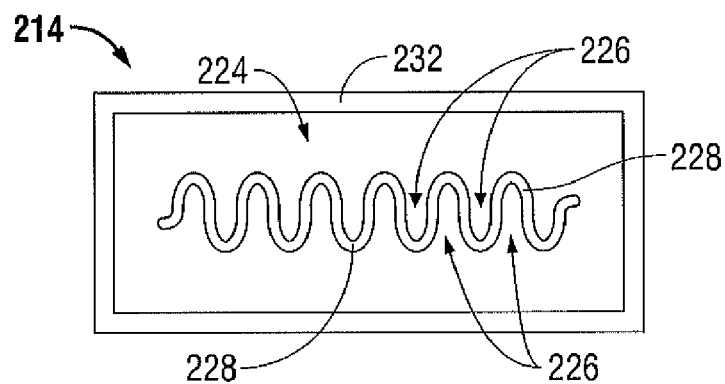
FIG. 5 a top view of still another embodiment of the retention device in accordance with the present disclosure.
Figure 6:
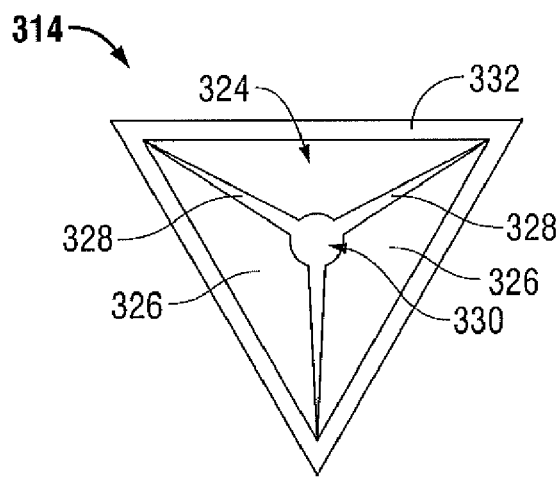
FIG. 6 a top view of yet another embodiment of the retention device in accordance with the present disclosure.

Referring now to FIGS. 4-6, other embodiments of a retention device 114, 214, and 314 are shown. FIG. 4 depicts a retention device 114 having a square-shaped membrane 124. Membrane 124 is provided with a central aperture 130 and a plurality of equally spaced slits 128 defined between membrane 124. Slits 128 extend outwardly from the central aperture 130 towards an outer bead 132 having a square shape to form a plurality of flexible segments 126 within membrane 124. Outer bead 132 is configured to secure membrane 124 within a housing (not shown) in a similar fashion as membrane 24 secures to housing 12 discussed above. Retention device 114 is configured to attach to a material "M" in a similar fashion as retention device 14 secures material "M" discussed above.

FIG. 5 depicts a retention device 214 having an elongated rectangular-shaped membrane 224. Membrane 224 is provided with serpentined pattern of equally spaced slits 228 running along the length of membrane 224. Slits 228 extend outwardly from membrane 224 towards an elongate outer bead 232 to form a plurality of flexible segments 226. Segments 226 are arranged in an opposing manner along membrane 224 and essentially act as a plurality of teeth to secure a material "M" to the connector 10. Elongate outer bead 232 is configured to secure membrane 224 within a housing (not shown) in a similar fashion as membrane 24 secures to housing 12 discussed above. Retention device 214 is configured to attach to a material "M" in a similar fashion as retention device 14 secures material "M" discussed above.

FIG. 6 depicts another embodiment of a retention device 314 having a generally triangular-shaped membrane 324. Membrane 324 is provided with a central aperture 330 and a plurality of equally spaced slits 328 that extend outwardly therefrom defined in material 324. Slits 328 extend outwardly from the central aperture 330 towards a triangular shaped outer bead 332 to form a plurality of flexible segments 326. Outer bead 332 is configured to secure membrane 324 within a housing (not shown) in a similar fashion as membrane 24 secures to housing 12 discussed above. Retention device 314 is configured to attach to a material "M" in a similar fashion as retention device 14 secures material "M" discussed above.

In the figures, namely, FIGS. 1-3, and the corresponding descriptions above, the retention device 14 of the connector bank assembly 10 has been described with the top portion 12a of housing 12 and the connector bank 16 has been described with the bottom portion 12b of the housing 12. However, this configuration, as described above, may be reversed and/or altered. Also, the retention device 14 has been described as being fixedly attached to the housing 12. This configuration may also be altered such that the retention device 14 may be detachable, monolithically formed within the housing 12a, for example, injection molded, glued, pressed, or any other suitable attaching means.

Although the foregoing disclosure has been described in some detail by way of illustration and example, for purposes of clarity or understanding, it will be obvious that certain changes and modifications may be practiced within the scope of the appended claims.

What is claimed:

1. A connector hub assembly, comprising:
   a housing having:
      a front side and a back side;
      a retaining ring disposed between the front and back sides;
      and a connector bank, the connector bank having at least one input port and at least one output port defined therein, the at least one input and output ports positioned along a same edge of the connector back, wherein the input and output ports allow fluid to flow therethrough; and
   retention device including a flexible membrane, the flexible membrane having an outer bead configured to secure the flexible membrane within the retaining ring of the housing, the flexible membrane having a plurality of slits defined therethrough that form a plurality of flexible segments in the membrane, the flexible segments configured to selectively secure the connector hub assembly to a sheet-like material when the sheet-like material is fed through at least one slit,
   wherein the slits are aligned radially,
   wherein the flexible segments allow the sheet-like material to be fed from a front side or a back side of the flexible membrane.

2. The connector hub assembly according to claim 1, wherein the housing includes a top portion and a bottom portion, wherein the top portion includes the retention device and the bottom portion includes the connector bank, wherein the input and output ports are positioned only along the same edge of the bottom portion.

3. The connector hub assembly according to claim 2, wherein the top portion and the bottom portion are monolithically formed into a one-piece configuration.

4. The connector hub assembly according to claim 2, wherein the top portion and the bottom portion are operably coupled by a coupling process selected from the group consisting of injection molding, gluing, snap fitting, hook and press forming.

5. The connector hub assembly according to claim 1, wherein the flexible membrane has a central aperture defining a plurality of slits, the slits extending radially outwards from the central aperture towards the outer bead to form a corresponding plurality of flexible segments for receiving the sheet-like material.

6. The connector hub assembly according to claim 5, wherein the flexible membrane is formed from a material selected from the group consisting of carbon fiber composites, plastic composites, flexible material composites, and epoxy composites.

7. The connector hub assembly according to claim 1, wherein the flexible membrane is selectively engageable with the housing.

8. The connector hub assembly according to claim 1, wherein the housing is constructed from a material selected from the group consisting of a plastic material and a metallic material.

9. The connector hub assembly according to claim 1, wherein the housing further includes a finger grip for manipulating the connector hub assembly.

10. The connector hub assembly according to claim 1, wherein the retention device is formed from a shape selected from the group consisting of a circular shape, a square shape, an elongate shape, a triangular shape, and a polygonal shape.

11. A connector hub assembly, comprising:
    a housing having a connector bank, the connector bank having at least one input port and at least one output port, wherein the at least one input port is configured to operably connect to at least one first conduit and the at least one output port is configured to operably connect to at least one second conduit, wherein the at least one input and output ports are positioned along a same edge of the connector back and allow fluid to flow therethrough; and
    a retention device including a flexible membrane having a central aperture defining a plurality of slits, the slits extending radially outwards from the central aperture towards an outer bead to form a corresponding plurality of flexible segments, wherein the retention device is coupled between a front side and a back side of the housing and configured to selectively secure the connector hub assembly to a sheet-like material when the sheet-like material is fed through the plurality of slits, wherein the flexible segments allow the sheet-like material to be fed from a front side or a back side of the flexible membrane.

12. The connector hub assembly according to claim 11, wherein the at least one first conduit and the at least one second conduit are selected from the group consisting of energy-transporting conduits, air-transporting conduits, and fluid-transporting conduits.

13. The connector hub assembly according to claim 11, wherein the at least one input port is operably connected to at least one first conduit and the at least one output port is operably connected to at least one second conduit by a type of connector selected from the group consisting of quick-release-type connectors, luer-type connectors, detent-type connectors, screw-type connectors, and bayonet-type connectors.

* * * * *